United States Patent

Shalon et al.

US005746725A

[11] Patent Number: 5,746,725
[45] Date of Patent: May 5, 1998

[54] CHECK VALVE AND METHOD FOR FACILITATING PRESSURIZATION OF A PATIENT'S MIDDLE EAR

[75] Inventors: Tadmor Shalon, Brentwood, Mo.; John J. Shea, Jr., Memphis, Tenn.

[73] Assignee: Metaphase Technology Access, Ltd., St. Louis, Mo.

[21] Appl. No.: 573,242

[22] Filed: Dec. 15, 1995

[51] Int. Cl.$^6$ .................................................. A61M 5/00
[52] U.S. Cl. ........................ 604/246; 604/247; 604/207; 606/108; 606/109
[58] Field of Search ........................ 604/48, 49, 54, 604/246, 247; 606/108, 109; 623/10; 128/898

[56] References Cited

U.S. PATENT DOCUMENTS

| | | |
|---|---|---|
| 3,730,181 | 5/1973 | Fling . |
| 3,749,083 | 7/1973 | Mathes, Jr. . |
| 3,916,873 | 11/1975 | Wasserman . |
| 4,031,569 | 6/1977 | Jacob . |
| 4,052,754 | 10/1977 | Homsy . |
| 4,094,303 | 6/1978 | Johnston . |
| 4,168,697 | 9/1979 | Cantekin . |
| 4,193,399 | 3/1980 | Robinson . |
| 4,274,162 | 6/1981 | Joy et al. . |
| 4,286,341 | 9/1981 | Greer et al. . |
| 4,326,512 | 4/1982 | Peerless . |
| 4,527,293 | 7/1985 | Eckstein et al. . |
| 4,534,761 | 8/1985 | Raible . |
| 4,568,337 | 2/1986 | Treharne, III et al. . |
| 4,650,488 | 3/1987 | Bays et al. . |
| 4,704,126 | 11/1987 | Baswell et al. . |
| 4,744,792 | 5/1988 | Sander et al. . |
| 4,808,171 | 2/1989 | Berger . |
| 4,888,017 | 12/1989 | DeVore et al. . |
| 5,053,040 | 10/1991 | Goldsmith, III . |
| 5,063,946 | 11/1991 | Wada . |
| 5,207,685 | 5/1993 | Cinberg et al. . |
| 5,246,455 | 9/1993 | Shikani . |

OTHER PUBLICATIONS

The Tympano–Frontal Shunt: A Procedure for the Treatment of Chronic Eustachian Tube Insufficiency; Goode and Glasscock; pp. 100–112, Laryngoscope, 1975.

*Physiology of the Eustachian Tube and Middle Ear Pressure Regulation*; Magnuson and Falk; Raven Press, NY; 1988; pp. 81–101.

*Regulation of Negative Middle Ear Pressure Without Tubal Opening*; Hergils and Magnuson; Arch Otolaryngol Head Neck Surg—vol. 114, Dec. 1988; pp. 1442–1444.

*Middle Ear as a Gas Pocket*; Sadé and Luntz; Ann Otol Rhinol Laryngol 99; 1990; pp. 529–534.

*A Biointegrated Hydroxylapatite Ventilation Tube for Definitive Treatment of Chronic Eustachian Tube Obstruction*; Jahn; Otolaryngoloy—Head and Neck Surgery, vol. 105, No. 5; pp. 757–760.

*Barotrauma in Boeing 737 Cabin Crew*; Kortschot and Oosterveld; ORL 1993;55; pp. 114–116.

*Middle Ear Symptoms While Flying*; Brown; Postgraduate Medicine, vol. 96 No. 2; Aug. 1994; pp. 135–142.

*Direct Demonstration of Gas Diffusion into the Middle Ear*; Herman, Luntz and Sadé; Acta Otolaryngol 1995; 115: pp. 276–278.

*Middle Ear Gas Composition and Middle Ear Aeration*; Sadé, Luntz, Levy; Ann Otol Rhinol Laryngol 104: 1995; pp. 369–373.

*Relationship Between the Gas Composition of the Middle Ear and the Venous Blood at Steady State*; Luntz, Levi, Sadé, Herman; Laryngoscope 105; May 1995; pp. 510–512.

*Pitch is Influenced by Differences in Gas Pressure Between the Middle Ear and the External Auditory Canal*; Fritze; Acta Otolaryngol 115; 1995; pp. 359–362.

*Primary Examiner*—Michael Powell Buiz
*Assistant Examiner*—Jennifer R. Sadula
*Attorney, Agent, or Firm*—Howell & Haferkamp, L.C.

[57] ABSTRACT

A check valve for providing fluid communication between a patient's middle ear and external auditory canal for improved comfort and hearing. The check valve is configured for permitting fluid to flow from the external auditory canal into the middle ear and for checking fluid flow from the middle ear to the external auditory canal.

12 Claims, 2 Drawing Sheets

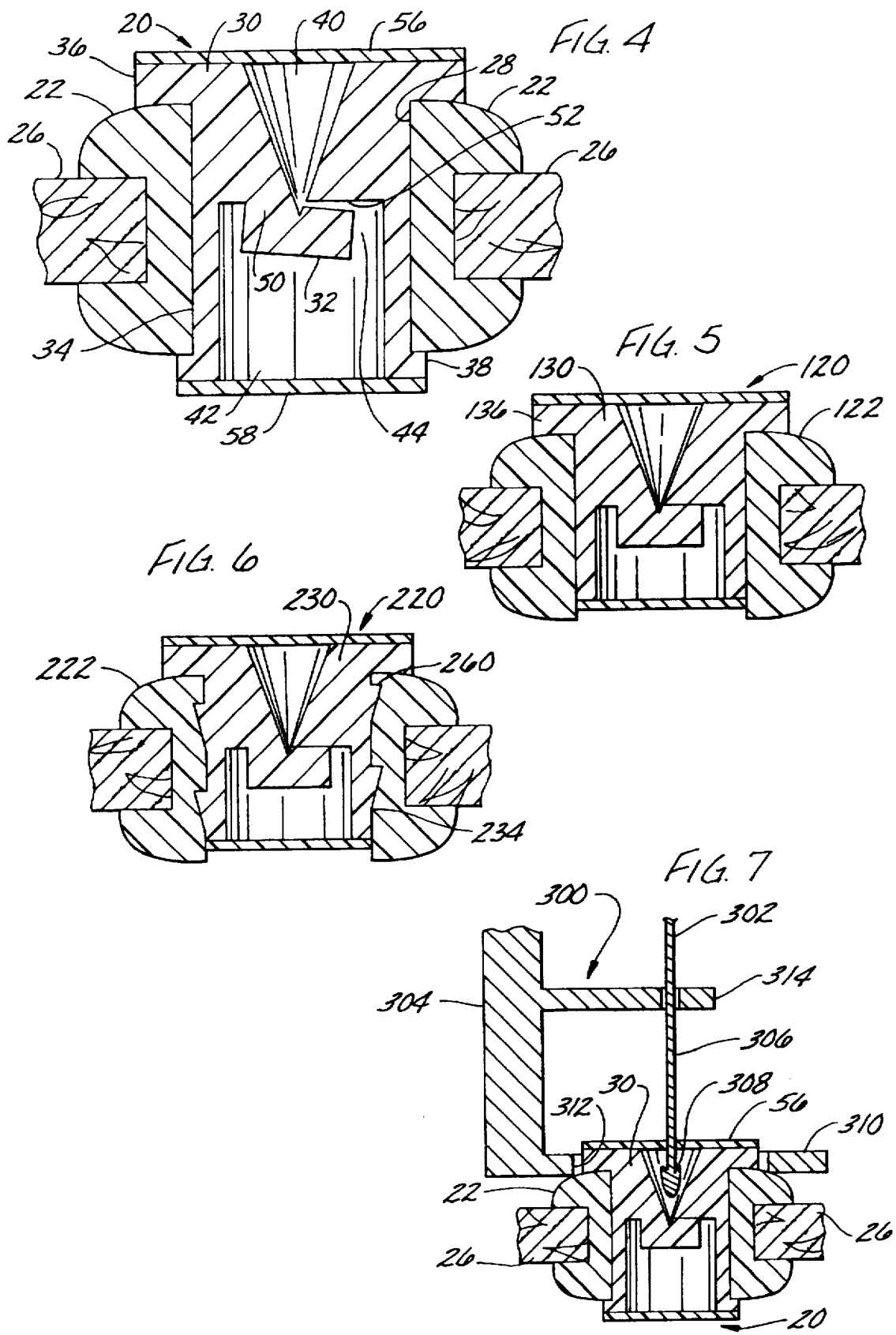

CHECK VALVE AND METHOD FOR FACILITATING PRESSURIZATION OF A PATIENT'S MIDDLE EAR

BACKGROUND OF THE INVENTION

This invention relates generally to methods and apparatus for pressurizing a patient's middle ear.

Middle ear negative pressure is frequently thought to result from a blockage of the Eustachian tube, which serves as a vent into the middle ear volume. Large negative pressures may lead to effusion of fluid into the middle ear volume and a retraction of the tympanic membrane.

Trans-tympanic ventilating tubes are commonly used for the prevention and treatment of middle ear negative pressure. Such tubes are generally inserted through the tympanic membrane to neutralize any pressure differential between the middle ear and the ambient atmospheric pressure within the patient's external auditory canal (i.e., ear canal). The use of trans-tympanic ventilating tubes is a common treatment for otitis media, an inflammation of the middle ear.

Pressurizing the middle ear through the Eustachian tube is another conventional technique for relieving negative middle ear pressure. This technique is capable of producing slight positive pressures relative to the ambient atmosphere. However, pressurizing the middle ear through the Eustachian tube requires a functional Eustachian tube.

The prior art has also addressed ventilation of the middle ear via a surgically implanted shunt that is employed for providing an air passageway between the middle ear and the frontal sinus. This shunt incorporates a passive valve at the middle ear end of the shunt tube which automatically opens when the middle ear reaches a small negative pressure. However, such procedure requires invasive surgery.

A disadvantage of the prior art techniques is they address only passive connections between the middle ear and the ambient atmosphere. They are not capable of actively controlling the pressure within the middle ear.

SUMMARY OF THE INVENTION

Among the several objects and features of this invention may be noted the provision of an improved apparatus and method for relieving negative pressure in a patient's middle ear; the provision of such apparatus and method for actively pressurizing the middle ear; the provision of such apparatus and method for facilitating active pressurization of the middle ear via the patient's ear canal; the provision of such apparatus and method for facilitating active pressurization of the middle ear without the need for any tools; the provision of such apparatus and method for facilitating active pressurization of the middle ear with hand or finger pressure; the provision of such apparatus which is of relatively simple construction; the provision of such apparatus and method which may be employed in a minimally invasive manner; the provision of such apparatus and method for facilitating comfortable and painless pressurization of the middle ear; and the provision of such apparatus which is compatible with commercially-available, implanted ventilating tubes.

Generally, a check valve of the present invention is employed for facilitating pressurization of a middle ear of a patient. The check valve is positionable in a passage between the middle ear and an external auditory canal of the patient. The check valve is configured for permitting fluid to flow from the external auditory canal into the middle ear and for checking fluid flow from the middle ear to the external auditory canal.

In another aspect of the present invention, the check valve comprises a valve body and a moveable portion. The valve body has an intake port, a discharge port, and a fluid passageway extending between the intake and discharge ports. The valve body is configured so that when the check valve is positioned in the patient, then (a) the intake port is in fluid communication with an external auditory canal of the patient and (b) the discharge port is in fluid communication with the middle ear. The moveable portion is configured for permitting fluid flow from the intake port to the discharge port via the passageway, and for checking against fluid flow from the discharge port to the intake port via the passageway.

In yet another aspect of the present invention, a method of pressurizing a middle ear of a patient comprises providing a check valve having an intake port, a discharge port, and a fluid passageway extending between the intake and discharge ports. The check valve is configured for permitting fluid flow from the intake port to the discharge port and for preventing fluid flow from the discharge port to the intake port. The check valve is then positioned in the patient so that the discharge port of the check valve is in fluid communication with the middle ear of the patient. Fluid pressure is then increased at the intake port of the check valve to a pressure greater than fluid pressure in the middle ear to cause fluid to flow through the check valve and into the middle ear.

In yet another aspect of the present invention, an extraction tool is employed for removing a valve positioned within a trans-tympanic ventilating tube extending through the tympanic membrane of a patient. The extraction tool comprises a puller rod and a pusher member. The puller rod is sized and configured for extending through the external auditory canal of the patient and for grabbing the valve to facilitate pulling of the valve out through the external auditory canal. The pusher member is sized and configured for extending through the external auditory canal of the patient and for engaging the trans-tympanic ventilating tube for applying a pushing force against the ventilating tube as the valve is pulled out of the ventilating tube via the puller rod to prevent removal of the trans-tympanic ventilating tube with the valve.

Other objects and features will be in part apparent and in part pointed out hereinafter.

BRIEF DESCRIPTION OF THE DRAWINGS

FIG. 4 is an enlarged sectional view similar to that of FIG. 2 but showing a valve flap of the valve in an open position;

FIG. 5 is an enlarged sectional view of another check valve of the present invention within a trans-tympanic ventilating tube;

FIG. 6 is an enlarged sectional view of yet another check valve of the present invention within a trans-tympanic ventilating tube; and FIG. 7 is a sectional view of an extraction tool of the present invention adjacent the valve of FIGS. 1–4.

Corresponding reference characters indicate corresponding parts throughout the several views of the drawings.

DESCRIPTION OF THE PREFERRED EMBODIMENT

Figure 1:
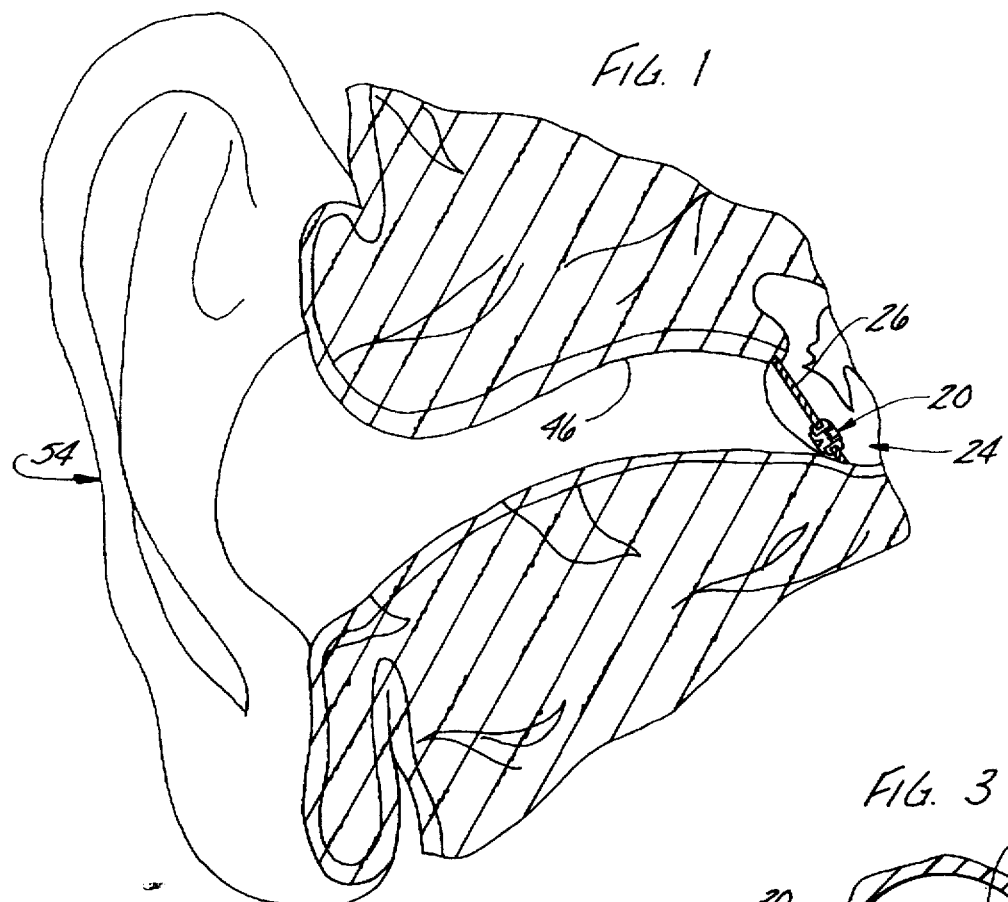
FIG. 1 is a sectional view of an ear of a patient showing a check valve of the present invention positioned in a trans-tympanic ventilating tube, the ventilating tube extending through the tympanic membrane of the patient's ear.
Figure 2:
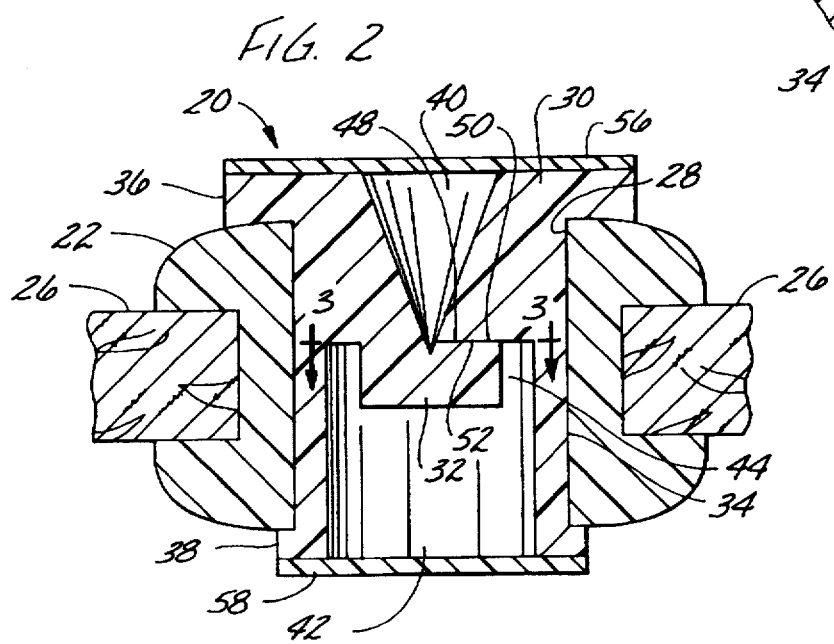
FIG. 2 is an enlarged sectional view of the check valve of FIG. 1.

Referring now to the drawings, and first more particularly to FIGS. 1 and 2, a check valve of the present invention is indicated in its entirety by the reference numeral 20. The check valve 20 is positioned within a conventional trans-tympanic ventilating tube (or rivet) 22 for facilitating pressurization of a middle ear 24 of a patient. As shown in FIG. 2, the ventilating tube 22 extends through the tympanic membrane 26 of the patient's ear. The ventilating tube 22 has a lumen 28, preferably with a diameter of approximately 1 mm.

The check valve 20 includes a valve body, generally indicated at 30, and a moveable portion (i.e., valve flap 32). Preferably, the valve body 30 and valve flap 32 are of a pliable, resilient, elastomeric material, such as a silicone rubber. An example of a suitable material is available from Dow Corning under the trademark Silastic®. The valve body 30 and flap 32 may be formed by any suitable method, such as machining, but are preferably formed by molding.

The valve body 30 has a generally cylindric tubular portion 34 sized (e.g., having a diameter of approximately 1 mm) for a snug fit in the lumen 28 of the trans-tympanic ventilating tube 22. First and second spaced flanges, 36, 38 extend radially outwardly from opposite ends of the tubular portion 34 of the valve body 30. Preferably, the flanges 36, 38 are spaced apart a distance substantially equal to the axial length of the trans-tympanic ventilating tube 22. The flanges 36, 38 are engageable with opposite ends of the trans-tympanic ventilating tube 22 for limiting axial movement of the check valve 20 relative to the ventilating tube. To insert the check valve 20 into the ventilating tube 22 when the tube is already positioned in the tympanic membrane 26 of the patient, the valve body 30 is resiliently compressed (or folded) and placed into the lumen 28 of the ventilating tube with forceps (not shown) or any other suitable tool. Upon removing the forceps, the valve body 30 expands (i.e., resiliently snaps) into position within the lumen 28 as shown in FIG. 2, with the flanges 36, 38 engaging the ends of the ventilating tube 22. Thus, a clinician may easily install the check valve 20 in a surgically implanted ventilating tube 22 in a quick and simple procedure.

The valve body 30 also has an intake port 40, a discharge port 42, and a fluid passageway 44 extending between the intake and discharge ports. The valve body 30 is configured so that when the check valve 30 is positioned in the trans-tympanic ventilating tube 22, the intake port 40 is in fluid communication with the external auditory canal (i.e., ear canal) 46 of the patient's ear, and the discharge port 42 is in fluid communication with the middle ear 24 of the patient's ear.

Figure 3:
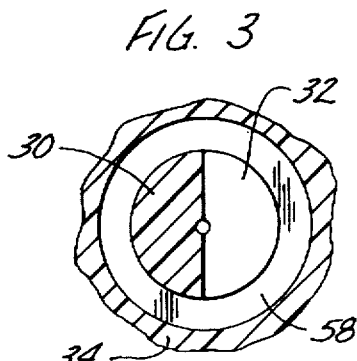
FIG. 3 is a cross-sectional view taken along the plane of line 3—3 of FIG. 2.

The check valve 20 includes a slit 48 between the valve flap 32 and valve body 30. The slit 48 defines an arcuate shaped sealing surface 50 (FIGS. 2–4) of the valve flap 32 adapted to sealingly engage a sealing surface 52 (FIGS. 2 and 4) of the valve body 30. The valve flap 32 is moveable between a first (open) position (shown in FIG. 4) and a second (closed) position (shown in FIG. 2). In the open position, the sealing surface 50 of the valve flap 32 is spaced from the sealing surface 52 of the valve body 30 to permit fluid flow (e.g., air flow) from the intake port 40 to the discharge port 42 via the slit 48 and passageway 44. In the closed position, the sealing surface 50 of the valve flap 32 sealingly engages the sealing surface 52 of the valve body 30 to prevent (or seal against) fluid flow from the discharge port 42 to the intake port 40 via the passageway 44. Preferably, the resiliency of the valve flap 32 and valve body 30 are such that the flap is biased in its closed position.

Because of the location of the flap 32 relative to the valve body 30, the flap and body permit fluid flow from the intake port 40 to the discharge port 42 via the passageway 44, and check (i.e., seal against) fluid flow from the discharge port to the intake port via the passageway 44. In other words, fluid is permitted to flow in only one direction (downward as viewed in FIGS. 2 and 4) through the check valve 20. When positioned in the trans-tympanic ventilating tube 22, the check valve 20 permits air to flow from the external auditory canal 46 into the middle ear 24, but checks air flow from the middle ear to the external auditory canal.

Because the resiliency of the valve flap 32 biases the flap in its closed position, the check valve 20 opens under an applied external positive pressure with respect to the middle ear 24. Without the application of an external positive pressure, the spring action of the flap 32 serves to move the flap to its closed position. An internal positive pressure, once achieved by inflation, further serves to close and seal the check valve 20. Moreover, a large negative middle ear pressure relative to ambient air pressure will also cause the flap 32 to move to its open position, thus relieving the negative pressure. Such large negative middle ear pressures are typically the reason for the initial insertion of the ventilating tube 22. Thus, because such negative pressures cause the flap 32 to move to its open position, the check valve 20 does not impair the designed function of the ventilating tube 22.

Preferably, only a very low activation or opening pressure is required to move the flap 32 to its open position to thereby open the check valve 20. Low activation pressure is desirable so that the patient does not have to provide a relatively high positive pressure in the external auditory canal 46 in order to allow passage of air into the middle ear 24. Preferably, the pressure necessary to open the check valve 20 is commensurate with the pressure such as can be achieved by cupping the hand over the pinna 54 of the ear (outer ear) and pressing inward. Such a low activation pressure ensures that large negative pressure cannot develop in the middle ear 24. A reduced middle ear pressure will activate the check valve 20 automatically to relieve the negative middle ear pressure when only a small pressure differential arises. Moreover, the resiliency of the valve flap 32 assures the check valve 20 of a low leakage rate through the slit 48 to minimize the frequency at which the patient must re-inflate the middle ear 24.

Referring again to FIGS. 2 and 4, the check valve 20 also preferably includes first and second hydrophobic membranes 56, 58 attached to opposite ends of the valve body 30. The hydrophobic membranes 56, 58 are preferably of polytetrafluoroethylene (Teflon®) and are air-permeable and water-impermeable for preventing passage of aqueous liquids while permitting the free transmission of gases through the membranes. The first (exterior) membrane 56 covers the intake port 40 of the valve body 30 for permitting passage of air from the external auditory canal 46 into the passageway 44 of the valve body, and for preventing passage of water from the external auditory canal into the passageway. The exterior membrane 56 serves to prohibit the ingress of liquids from the external auditory canal 46, thereby reducing the risk of middle ear infection. The second (interior) membrane 58 covers the discharge port 42 of the valve body 30 for permitting passage of air from the passageway 44 of the valve body into the middle ear 24, and for preventing passage of aqueous liquids from the middle ear 24 into the passageway. The interior membrane 58 serves to protect the check valve 20 from occlusion by any exudate of the middle ear 24, if present. Such liquids might restrict the action of the check valve 20. Although the check valve 20 preferably has both the interior and exterior membranes 56, 58, it is to be understood that a check valve 20 may alternatively have no such membranes or only one membrane without departing from the scope of this invention.

Although the check valve 20 is described as being insertable into a trans-tympanic ventilating tube 22 surgically implanted in a passage in the tympanic membrane 26, it is to be understood that the check valve 20 could alternatively be positioned within another passage which provides fluid communication between the external auditory canal 46 and middle ear 24. For example, the check valve 20 could alternatively be inserted into a shunt tube (not shown) surgically implanted through the attic bony canal wall near the external auditory canal 46 and in fluid communication with the middle ear volume.

After the check valve 20 is installed in the surgically implanted ventilating tube 22, it may be operated by the patient (or by another person if the patient is a small child or otherwise unable to operate the valve) to pressurize the middle ear 24. The patient's middle ear 24 may be pressurized by cupping a hand over the outer ear in a substantially airtight seal, and then gently pressing inwardly (i.e., flattening the hand while pressing inward on the pinna 54). This pumping motion compresses the air within the volume of the pinna 54 and external auditory canal 46. This compressed air forces the valve flap 32 to its open position thereby allowing the compressed air to flow through the check valve 20 and into the middle ear 24. When the pressures within the middle ear 24 and external auditory canal 46 equalize, or when the hand pressure on the ear is released, then the valve flap 32 springs back to its closed position to seal the compressed air within the middle ear. Thus, the middle ear 24 may be pressurized to a slight positive pressure (i.e., a pressure greater than ambient pressure) without the need for any external device. This allows the patient to comfortably and discretely inflate his/her middle ear 24 whenever pressurization is desired (e.g., whenever the patient notices a degradation in hearing and/or a sensation of blockage in the ear). The ability to discretely operate the check valve 20 as needed encourages compliance in its use by the patient. Also, because the middle ear 24 is inflated by hand pressure, there is almost no risk of overinflation.

Alternatively, the patient may place a finger over the external auditory canal 46 and press or pump inward, again pressurizing the air in the external auditory canal 46 and activating the check valve 20. Alternatively, the patient may apply pressure to the tragus (cartilage flap) at the entrance to the external auditory canal 46 and press inward, again producing the pumping action. Optionally and less desirably, a bulb or other kind of pressurizing device could be used to pressurize the air in the external auditory canal 46.

An important benefit of the check valve 20 is that its performance and the patient's use of the valve may be easily verified in a clinical office. A simple testing procedure is described which can be used to ensure that the check valve 20 has been properly installed in the ventilating tube 22 immediately following the insertion procedure. In addition, this testing method may be used to educate the patient in the proper inflation procedure described above.

To test whether the check valve 20 is functioning properly, the external auditory canal 46 is sprayed, or filled, with a test gas. Suitable gases for this purpose include Refrigerant 22 and other inert gases which do not occur in abundance in the atmosphere. Once the external auditory canal 46 is filled with the test gas, the patient or clinician performs the inflation procedure described above, activating the check valve 20 and pumping the test gas into the middle ear 24. The middle ear volume is now inflated with the test gas. The external auditory canal 46 is then purged with ambient air to remove any residual test gas. To test for leakage, the external auditory canal 46 is then probed with a suitable gas phase leak detector to detect any gas leakage. Such detectors are well known in the art, e.g. Robinair Model 16500 Electronic Leak Detector used to detect small Refrigerant 22 leaks. Other types of leak detectors, such as mass spectrometers, are known in the art and suitable for this testing. The external auditory canal 46 may be monitored over a period of time to look for leakage back through the check valve 20.

This same testing method may be used to assist the clinician in educating the patient in the proper use and operation of the check valve 20. The external auditory canal 46 is filled with the test gas and the patient is instructed to inflate the middle ear 24 by pumping. Proper pumping action will greatly reduce the test gas concentration in the external auditory canal 46 because some of the test gas will flow to the middle ear 24. High concentrations of the test gas following attempted inflation by the patient may indicate that the check valve 20 has not been activated. By monitoring the test gas concentration before and after inflation by the patient, the patient may be taught the optimal method for inflation. This unique feature allows the patient and clinician to refine the pumping procedure as needed for efficiency and patient comfort.

A second embodiment of a check valve, generally indicated at 120, is shown in FIG. 5 secured to a trans-tympanic ventilating tube 122. The valve 120 is similar to the check valve 20 of FIGS. 2–4 except it does not have a second flange. The valve 120 is secured to the ventilating tube 122 with a suitable adhesive (not shown), such as 3M Medical Adhesives, which are known in the art and are accepted as medically safe. Preferably, such adhesive is positioned between a flange of the ventilating tube and the flange 136 of the valve body 130.

A third embodiment of a check valve, generally indicated at 220, is shown in FIG. 6 secured to a trans-tympanic ventilating tube 222. The check valve 220 is similar to the check valve 120 of FIG. 5, except the tubular portion 234 of the check valve body 230 includes an external screw thread 260. The valve body 230 of the check valve 220 is preferably molded with the thread 260. Use of this type of check valve requires a ventilating tube having a threaded lumen for receiving the valve body.

The check valve 120 and check valve 220 function and operate in the same manner as check valve 20, described above. The detailed discussion of the check valve 20 is equally applicable to the check valves 120 and 220 and, therefore, it is unnecessary to discuss valves 120 and 220 in further detail.

Referring now to FIG. 7, the check valve 20 may be removed from the trans-tympanic ventilating tube 22 via an extraction tool, generally indicated at 300. The extraction tool 300 comprises a puller rod 302 and a pusher member, generally indicated at 304.

The puller rod 302 has a generally elongated shaft 306 and a barb 308 at one end of the shaft. The shaft 306 and barb 308 are sized and configured for extending through an external auditory canal 46 of the patient and grabbing the valve to facilitate pulling of the valve out through the external auditory canal 46. In particular, the barb 308 is shaped for piercing the exterior (upper as viewed in FIG. 7) hydrophobic membrane 56 and for forcing open the valve to permit the barb 308 to pass through the valve. As the puller rod 302 is extracted, the barb 308 grabs either the valve body 30 or the flap 32 so that the check valve 20 is extracted with the puller rod 302.

The pusher member 304 is sized and configured for extending through the external auditory canal of the patient and engaging the trans-tympanic ventilating tube 22 for allowing the operator to apply a pushing force against the ventilating tube as the valve is pulled out of the ventilating tube via the puller rod 302. In particular, the pusher member 304 includes a foot plate 310 at its distal end for engaging the ventilating tube 22. A hole 312 through the foot plate 310 is sized for passage of the check valve 20 therethrough. By pushing against the ventilating tube 22 during extraction of the check valve 20, the pusher member 304 prevents removal of the ventilating tube with the check valve. This prevents damage to the tympanic membrane 26 which might be caused by pulling on the combined valve body 30 and ventilating tube 22, and also minimizes any discomfort for the patient during the removal procedure. Preferably, the pusher member 304 includes a guide 314 for guiding the puller rod 302 into engagement with the check valve 20.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense. It is intended that the specification, together with the following example, shall be considered exemplary only, with the invention being limited solely by the scope of the claims which follow the example.

EXAMPLE

A preliminary version of the check valve has been tested. An adult patient was fitted with a trans-tympanic ventilating tube and valve to maintain a positive pressure in the middle ear. The valve was formed by making several slits in an elastomeric tube which also functioned as the ventilating tube. The patient's hearing was tested before and after the insertion of the tube and valve. The patient was able to pressurize his middle ear via hand pressure after the valve was inserted. The patient pressurized his middle ear through the tube and valve combination several times a day for comfort and improved hearing. Hearing tests document a dramatic improvement in the ear with the tube and valve. Low frequency response was particularly improved. Improvement was significant enough that the patient no longer required a hearing aid. No complications due to the use of the valve were reported. The improved versions of the active middle ear ventilating valve described above will produce similar results, with enhanced ease of use.

What is claimed is:

1. A method of pressurizing a middle ear of a patient comprising:

providing a check valve having an intake port, a discharge port, and a fluid passageway extending between the intake and discharge ports, said check valve being configured for permitting fluid flow from the intake port to the discharge port and for preventing fluid flow from the discharge port to the intake port; and positioning the check valve in the patient so that the discharge port is in fluid communication with said middle ear of the patient.

2. A method as set forth in claim 1 wherein the step of positioning the check valve in the patient comprises positioning the check valve in a passage through a tympanic membrane of the patient so that the intake port of the check valve is in fluid communication with an external auditory canal of the patient and the discharge port of the check valve is in fluid communication with the middle ear of the patient.

3. A method as set forth in claim 2 wherein the step of positioning the check valve through said tympanic membrane comprises connecting the check valve to a trans-tympanic ventilating tube extending through said tympanic membrane.

4. A method as set forth in claim 1 wherein the step of positioning the check valve in the patient comprises positioning the check valve in a passage extending between the middle ear and an external auditory canal of the patient so that the intake port of the check valve is in fluid communication with an external auditory canal of the patient and the discharge port of the check valve is in fluid communication with the middle ear of the patient.

5. The method of pressurizing the middle ear of a patient as set forth in claim 1, further comprising:

increasing fluid pressure at the intake port of the check valve to a pressure greater than fluid pressure in the middle ear to cause fluid to flow through the check valve and into the middle ear.

6. A method as set forth in claim 5 wherein the step of positioning the check valve in the patient comprises positioning the check valve in a passage extending between the middle ear and an external auditory canal of the patient so that the intake port of the check valve is in fluid communication with an external auditory canal of the patient and the discharge port of the check valve is in fluid communication with the middle ear of the patient.

7. A method as set forth in claim 6 wherein the step of increasing fluid pressure comprises compressing air within the external auditory canal, said compression of air causing air to flow through the check valve and into the middle ear.

8. A method as set forth in claim 6 wherein the step of increasing fluid pressure comprises covering an outer ear of the patient with a hand and pressing thereon to compress the air within the external auditory canal, said compression of air causing air to flow through the check valve and into the middle ear.

9. A method as set forth in claim 6 wherein the step of increasing fluid pressure comprises pressing the cartilage flap at the entrance to the external auditory canal inward into the external auditory canal to compress the air within the canal, said compression of air causing air to flow through the check valve and into the middle ear.

10. A method as set forth in claim 6 wherein the step of increasing fluid pressure comprises placing a finger into the entrance of the external auditory canal and pushing the finger inward into the canal to compress the air within the canal, said compression of air causing air to flow through the check valve and into the middle ear.

11. A method as set forth in claim 6 wherein the step of increasing fluid pressure comprises compressing a test gas within the external auditory canal to cause the test gas to flow through the check valve and into the middle ear, said method further comprising placing a gas detector into the external auditory canal of the patient to determine whether the test gas is present in the external auditory canal.

12. A method of extracting a valve from a trans-tympanic ventilating tube in a tympanic membrane of a patient, said method comprising:

pushing against the trans-tympanic ventilating tube while simultaneously pulling on the valve to separate the valve from the trans-tympanic ventilating tube without removing the trans-tympanic ventilating tube from the tympanic membrane.

\* \* \* \* \*